United States Patent [19]
Becker et al.

[11] Patent Number: 5,993,811
[45] Date of Patent: Nov. 30, 1999

[54] METHOD AND COMPOSITIONS FOR PREVENTING AND TREATING THE SYSTEMIC INFLAMMATORY RESPONSE SYNDROME INCLUDING SEPSIS

[75] Inventors: Kenneth L. Becker, Washington, D.C.; Jon C. White, Chevy Chase, Md.; Eric S. Nylen, Bethesda, Md.; Richard H. Snider, Jr., Upper Marlboro, Md.

[73] Assignee: Biology Associates, LLC, Bethesda, Md.

[21] Appl. No.: 08/794,740

[22] Filed: Feb. 3, 1997

[51] Int. Cl.$^6$ ................................................. A61K 39/395
[52] U.S. Cl. .................................. 424/130.1; 424/139.1; 424/144.1; 424/142.1; 424/158.1; 424/178.1
[58] Field of Search ........................... 424/130.1, 139.1, 424/141.1, 142.1, 158.1, 178.1

[56] References Cited

U.S. PATENT DOCUMENTS

| | | |
|---|---|---|
| 4,277,393 | 7/1981 | Sakakibara et al. . |
| 4,493,795 | 1/1985 | Nestor, Jr. et al. . |
| 5,330,909 | 7/1994 | Yamashita et al. . |
| 5,639,671 | 6/1997 | Bohvon . |

OTHER PUBLICATIONS

Hamilton G, et al., *Scand. J. Infect. Dis.*, 1992; 24:361.
Bone RC, *Crit. Care Med.* 1996; 24:163.
Burrell R, *Circ. Shock*, 1994; 43:137.
Bahrami S, et al., *Prog. Clin. Biol. Res.*, 1995; 392:197.
American College of Chest Physicians/Society of Critical Care Medicine Consensus Conference, *Crit. Care Med.*, 1992; 20:864.
Bone RC, *JAMA*, 1995; 273:155.
Rangel–Fausto MS, et al., *JAMA*, 1995; 273:117.
Centers for Disease Control, *MMWR*, 1990; 39–31.
Lowry SF, *Crit. Care Med.*, 1994; 22:S1–2.
Grabosch R, et al., *Burns*, 1992; 18:113.
Becker KL, et al., *Anat. Rec.*, 1993; 236:136.
Becker KL, et al., "The Pathophysiology of Pulminary Calcitonin," in *The Endocrine Lung in Health & Disease*, Becker et al, Eds., W.B. Saunders, Philadelphia, pp. 277–299, 1984.
Snider, R et al., "Characterization of the hyperprocalcitonemia of inflammatory/infectious disorders," Am. Fed. Clin. Res., New Orleans, LA, Feb. 1, 1996.
Sperber SJ, et al., *Rev. Inf. Dis.*, 1990; 12:736.
White J., et al, *Pancreas Club*, San Francisco, CA May 19, 1996.
O'Neill W., et al, *J. Burn Care Rehab.*, 1992; 13:605.
Nylen ES, et al., *Respir Med*, 1995; 89:41.
Zeigler, EJ, et al, *New Engl. J. Med.*, 1991; 324–429.
Natanson, C, et al., *Ann Int Med*, 1994; 120:771.
Suffredini, AF, *Crit. Care Med.*, 1994; 22:S12.
Fisher, CJ, et al, *New Eng. J. Med.*, 1996; 334:1697.
Eipper BA, et al., *Annu. Neurosci.*, 1992; 15:57.
Becker KL, et al., in *Principles and Practice of Endocrinology and Metabolism*, 2$^{nd}$ ed., Becker KL, Ed., JB Lippincontt Co., Philadelphia, 1995, p. 474.

LeMoullec JM, et al., *FEBS Lett*, 1984; 167:93.
Mostov KE, *Histol. Histopathol.*, 1995; 10:423.
Rothman JE, et al., *FASEB J.*, 1990; 4:1460.
Steiner DF, et al., *J. Biol. Chem.*, 1992; 267:23435.
Treilhou–Lahille F, et al., *Biology of the Cell*, 1986; 57:221.
Becker, KL, et al., Procalcitonin and its constituent peptides circulate in normal persons, 15$^{th}$ Joint Meeting of British Endocrine Societies, Dublin Ireland, Mar. 26, 1996.
Becker KL, et al., *Acta Endocrinol.*, 1978; 89:89.
Becker KL et al., *Surg. Gynecol. Obstet.*, 1982; 154:897.
Guilloteau D, et al., *J. Clin. Endocrinol. Metab.*, 1990; 71:1064.
Motté P, et al., *Clin. Chim. Acta.*, 1988; 174:35.
Seth R, et al., *Horm. Metab. Res. Suppl.*, 1989; 21:3.
Weissel M, et al., *Acta Endocrinol.*, 1991; 124:540.
Becker KL, et al., in *Comparative Respiratory–Tract Carcinogenesis*, Reznick–Schuller H, Ed., CRC Press, Boca Raton, FL, 1984; p. 161.
Becker KL, et al., *Biochem. Pharmacol.*, 1985; 34:155.
Dandona, P. et al., J. Clin. Endocrinol. Metab., 79:1605–08, 1994.
Nylen, ES et al., Crit. Care Med., 25(8):1362–5, 1997.
Pahlke, K. et al., *Intensivmedizin und Notfallmedizin*, 34(5):381–387, 1997, Biosis Abstract Only, Accession No. 99708284.
Christman, JW et al., *Critical Care Medicine*, 23(5):955–963, 1995.
Quezado, ZMN et al., *Trends in Biotechnology*, 13(2):56–63, 1995.
Eichacker, PQ et al., *Intensivmedizin und Notfallmedizin*, 34(2):101–109.
Nylen, ES et al., *Am. J. Med. Sci.*, 312(1):12–18, 1996.
Lynn WA et al., *Clin. Infect. Dis.*, 20(1):143–58, 1995.
Becker KL et al., *J. of Endocrinology*, 152(Suppl), Abstract P145.
Mohamadi et al, "Paradoxical Effect of Parathyroid Hormone and Calcitonin on Serum Calcium in Man", pp. 657–660.
Silva et al, *Geriatrics*, vol. 28, p. 178(1973).
Silva et al, *Arch. Intern. Med.*, vol. 132, pp. 337–339 (1973).
Wisneski et al, *Clin. Pharmacol. Ther.*, vol. 24 (2), pp. 219–222 (1978).
Mohamadi et al, *Acta Endocr.*, vol. 79, pp. 700–708 (1975).
Nylen et al, *Crit. Care Med.*, vol. 26 (6), pp. 1001–1006 (1998).
Silva et al, *Lancet*, vol. 20, p. 763 (1972).
"Cibacalcin" from the *Physicians' Desk Reference*, pp. 889–890 (1993).

(List continued on next page.)

*Primary Examiner*—Marianne P. Allen
*Attorney, Agent, or Firm*—Oblon, Spivak, McClelland, Maier & Neustadt, P.C.

[57] ABSTRACT

Administration of an antibody reactive to procalcitonin and/or its components is effective for the treatment and/or prevention of systemic inflammatory response syndrome (SIRS) and sepsis.

26 Claims, 2 Drawing Sheets

OTHER PUBLICATIONS

"Calcimar" from the *Physicians' Desk Reference*, pp. 1910–1911 (1993).
R. C. Bone et al, in *Critical Care Medicine*, vol. 17, pp. 389–393 (1989).
R. C. Bone in *Infectious Disease Clinics of North America*, vol. 5, pp. 793–805 (1991).
S. Rangel–Frausto et al, *JAMA*, vol. 273, pp. 117–123 (1995).
C. Brun–Buisson et al, in *JAMA*, vol. 274, pp. 968–974 (1995).
R. C. Bone et al, in *Critical Care Medicine*, vol. 23, pp. 994–1006 (1995).
*Sepsis and Multiorgan Failure*, Alan M. Fein et al, Eds., William & Wilkins, Baltimore, pp. 1 and 8, 1997.
Mastorakos G, et al., *J. Clin. Endocrinol. Metab.*, 1994; 79:934.
Schutze, S, et al., *Immunobiology*, 1995; 193:193.
Madara JL, et al., *J. Clin. Invest.*, 1989; 83;724.
Krieger DT, *Clin. Res.*, 1983; 31:342.
LeRoith D, et al., *Adv. Metabolic Disorders*, 1983; 10:303.
Dunne, JR, et al., *J. Surg. Res.*, 1996; 61:348.
Steinwald, P, et al., Intl. Congress Endocrinology, San Francisco, CA, Jun. 1996.
Becker KL, *Chest*, 1981; 79:211.
Kelley MJ, *Am J Respir Crit Care Med*, 1994; 149:183.
Chen D, et al., *Biochem Pharmacol*, 1995; 49:1623.
Abdullah SE, et al., *Agents Actions*, 1977; 7:533.
Aida S, et al., *Ann Rheum Dis*, 1994; 53:247.
Clopath P, et al., *Prostaglandins*, 1980; 19:1.
Edvinsson L, et al., *J Cereb Blood Flow Metab*, 1987; 7:720.
Silva OL, et al., *Clin Chem*, 1974; 20:337.
Silva OL, et al., *Am J Med Sci*, 1978; 275:159.
Becker KL, et al., *Acta Endocrinol*, 1979; 92:746.
Becker KL, et al., *Experientia*, 1980, 36:609.
Tashjian AH, et al., *N Engl J Med*, 1970; 283:890.
Snider RH, et al., *Clin Chim Acta*, 1977; 76:1.
Becker KL, et al., *Cancer Lett*, 1983; 18:179.
McMahon JL, et al., *Lung*, 1984; 162:261.
Becker KL, et al., *Arch Pathol Lab Med*, 1980; 104:196.
Nylen ES, et al., *Peptides*, 1987; 8:977.
Zhou A, et al., *J Biol Chem*, 1993; 286:1763.
Nylen ES, et al., *Acta Physiol Scand*, 1988; 132:117.
Linnoila RI, et al., *Lab Invest*, 1984; 51:39.
Aduen J, et al., *Crit Care Med*, 1995; 23–246.
Zaloga GP, et al., *Ann Surg*, 1985; 202:587.
Goldstein RA, et al., *Univ Karlova Publ.* Prague, 1971, p. 315.
Mohamadi M, et al., *Acta Endocrinol*, 1975; 79:700.
Gattereau A, et al., *J Clin Endocrinol Metab*, 1980; 51:354.
Gennari C, et al., *Curr Therap Res*, 1981; 30:1024.
Tabassian A, et al., *Life Sciences*, 1988; 42:2323.
Alam ASMT, et al., *J. Endocrinol*,1993; 136:7.
Salem M, et al., *Crit Care Clin*, 1991; 7:225.
Palmieri GM, et al., *Endocrinology*, 1969; 84:1509.
Weglicki WB, et al., *Molec Cell Bioch*, 1992; 110:169.
Yajnik CS, et al., *BMJ*, 1984; 288:1032.
Salem M, et al., *Crit Care Med*, 1995; 23:108.
Minne H, et al., *Acta Endocrinol*, 1973; Suppl 173:162.
Cantalamessa L, et al., *Metabolism*, 1978; 27:987.
Yamaguchi M,, *Endocrinol Jpn*, 1981; 28:643.
Hirata Y, et al., *J Clin Endocrinol Metab*, 1996; 81:1449.
Sugo S, et al., *Biochem Biophys Res Commun*, 1995; 207:25.
Nelkin BD, et al., *Biochem Biophys Res Commun*, 1984; 123:648.
Nuovo GJ, *PCR in situ Hybridization*, Raven Press, NY; Ch 5, 1992.
Knaus AW, et al., *Crit Care Med*, 1985; 13:818.
Colt EW, et al., *Am J Clin Path*, 1971; 55:40.
Gravel MR, et al., *J. Bone Min Res*, 1994; 9:1769.
Kelley M, et al., *Cancer Lett*, 1994; 81:19.
Selawry HP, et al., *Horm Metab Res*, 1975; 7:432.
Burgess TL, et al., *Ann Rev Cell Biol*, 1987; 3:243.
Becker KL, et al., "Calcitonin: Stricture, Molecular Biology, and Actions," in *Principles of Bone Biology*, Academic Press, New York, pp. 471–494, 1996.
Snider, Jr., et al, *J. Investig. Med.*, 45:552–560 (1997).
Bedu et al, *Serum Procalcitonin in Neonatal Sepsis*, 37th ICAAC, Toronto, Canada, (1997).
Chiesa et al, *Procalcitonin (PCT) as a Marker of Late–Onset Neonatal Infection*, 37th ICAAC, Toronto, Canada (1997).
Oberhoffer et al, *Clin. Intensive Care* (Suppl.), 7:46 (1996).
de Werra et al, *Crit. Care Med.*, 25:607–613 (1997).
Linnoila et al, *Clinical Research*, 30(1):434A (1982).
Christman et al, *Crit. Care Med.*, 23:995–963 (1995).
Al–Nawas et al, *Eur. J. Med. Res.*, 1:331–333 (1996).
Lynn et al, *Clin. Infect. Dis.*, 20:143–58 (1995).
Eichacker et al, *Intensivmed* 34:101–109 (1997).
Davis et al, *Trans. Roy. Soc. Trop. Med. Hyg.*, 88:670–671 (1994).
Gérard et al, *Infection*, 23:310–311 (1995).
Miller et al, *Am. Rev. Respir. Dis.* 140:283–284 (1989).
Tabassian et al, *Am. Rev. Respir. Dis.* 140:436–440 (1989).
Zeni et al, Serum Procalcitonin (PC) in Sepsis: Relation to Severity and Cytokines (TNF, IL–6,m IL–8), ICAAC, Orlando, Florida, (1994).
Becker et al, *Pulmonary Neuroendocrine Cell–Derived Calcitonin and Gastrin–Releasing Peptide in Inhalational Burn Injury*, 72nd Annual Endocrine Society Meeting, Atlanta, Georgia (1990).
Mol et al, *Regulatory Peptides*, 35:189–195 (1991).
Nylen et al, *Procalcitonin: A Causal Factor of Sepsis Mortality Fulfilling the Koch–Dale Mediator Criteria*, 37th ICAAC, Toronto, Canada (1997).
Grecka et al, *Plasma Procalcitonin (PCT) as a Parameter of Infection in Febrile Neutropenic (NF) Patients*, 37th ICAAC, Toronto, Canada (1997).
Nylen et al, *Crit Care Med.*, 25:1362–1365 (1997).
Al–Nawas et al, *Eur. J. Med. Res.*, 2:206–208 (1997).
Becker et al, *La Procalcitonin: Implication Dans La Mortalite Par Choc Septique*, XV$^e$ Congres de la Societe Francaise d'Endocrinologie (997).
Saadia, *Br. J. Surg.*, 82:1243–1244 (1995).
Skolnick, *JAMA*, 264:565–566 (1990).
Dana et al, *Endocrinol.*, 126:672–674 (1990).
Quezado et al, *TIBTECH*, 13:56–63 (1995).
Staehler et al, *Transplantation Proceedings*, 29:584–585 (1997).
Linnoila et al, *Anat. Rec.*, 236:231–240 (1993).
Nylen et al, *Altered Molecular Heterogeneity of Serum Calcitonin—An Index of Inhalational Burn Injury*, American Burn Association 23rd Annual Meeting (1991).
Brunkhorst et al, *Early Identification of Biliary Pancreatitis with Procalcitonin—A New Inflammatory Parameter*, 4th United European Gastroenterology Week—50th Annual Meeting of the German Society of Gastroenterology and Metabolism, Berlin, Germany (1995).

Al–Nawas et al, *Infection*, 24:434–436 (1996).
Nylen et al, Pneumonitis–Associated Hyperprocalcitonemia, American Thoracic Society (1994).
Lind et al, *Intensive Care Med.* 21:63–66 (1995).
Whang et al, Prognostic Value of Serum Procalcitonin Levels in SIRS, Endocrine Society Meeting, Minneapolis, Minnesota (1997).
Smith et al, *Clin. Infect. Dis.*, 20:641–645 (1995).
Nylen et al, *Am. J. Med. Sci.*, 312:12–18 (1996).
Steinwald et al., *Crit. Care Med.*, 25(Suppl.):278 (1997).
Becker et al, *The Hyperprocalcitonemia of Severe Infections: Associated Secretion of Other Constituents of the Prohormone*, Endocrine Society Meeting, 77th Annual Meeting, Washington, D.C. (1995).
Nylen et al, *Anat. Rec.*, 236:248–252 (1993).
Assicot et al, *The Lancet*, 341:515–518 (1993).
Tabassian et al, *Anat. Rec.*, 236:253–256 (1993).
Tabassian et al, *Experimental Lung Research*, 16:267–277 (1990).
Nylen et al, *Anat. Rec.*, 236:129–135 (1993).
Nylen et al, *Am. J. Respir.*, 2:25–31 (1990).
Nylen et al, *Horm. metab. Res.*, 24:439–442 (1992).
Becker et al, *Hyperprocalcitonemia as a Clinical Marker for Systemic Inflammation*, ICAAC, New Orleans, Louisiana (1996).
Pahlke et al, *Intensivmedizin und Notfallmedizin*, 34:381–387 (1997).
Hammer et al, *Clin. Intensive Care*, 7:39 (1996).
Nylen et al, *Procalcitonin–Reactive Antiserum Decreases Mortality from Sepsis*, IBC Conference, Sepsis, Washington, D.C. (1997).
Snider, Jr., et al, *J. Investig. Med.*, 44:47A (1996).
Becker et al, *Preferential Hypersecretion of Procalcitonin and its Precursors in Peneumonitis: A Cytokine–Inducted Phenomenon?*, Endotoxemia and Sepsis National Meeting, Philadelphia, Pennsylvania, (1995).
Whang et al, *nProCT, the Amino–Terminus of Procalcitonin, Correlates with the Progression of the Systemic Inflammatory Response Syndrome (SIRS)*, ICAAC, Toronto, Canada (1997).
Bone et al, *Chest*, 101:1644–1655 (1992).
Michie, *World J. Surg.*, 20:460–464 (1996).

METHOD AND COMPOSITIONS FOR PREVENTING AND TREATING THE SYSTEMIC INFLAMMATORY RESPONSE SYNDROME INCLUDING SEPSIS

The United States Government retains a nonexclusive, irrevocable, royalty-free license in this invention.

BACKGROUND OF THE INVENTION

1. Field of the Invention

The present invention relates to a method for preventing and/or treating the clinical illness currently termed systemic inflammatory response syndrome (SIRS) including sepsis (SIRS/sepsis). The present invention also relates to pharmaceutical compositions useful for the prevention and/or treatment of SIRS/sepsis.

2. Discussion of the Background

Inflammation, a component of host protection, is the composite, successive events in response to an injury that may be infectious or non-infectious. Inflammation involves a wide variety of physiologic, cellular and molecular events, including vasodilatation; increased vascular permeability; extravasation of plasma leading to interstitial edema; chemotaxis of neutrophils, macrophages and lymphocytes; activation of complement; and stimulation of antibodies.

Important proximal mediators of this response include two inflammatory cytokines, interleukin-1β (Il-1β) and tumor necrosis factor alpha (TNFα) (Hamilton G, et al., *Scand. J. Infect. Dis.*, 1992; 24:361; and Bone R C, *Crit. Care Med.* 1996; 24:163). They are produced primarily by macrophages, assist beneficially in the local inflammatory response, and act in conjunction with other cytokines, prostaglandins, leukotrienes, complement, histamine, serotonin, substance P, and other mediators.

Bacterial infection and other potent stimuli often initiate a marked augmentation of pro-inflammatory cytokines that results in systemic inflammation (Burrell R, *Circ. Shock*, 1994; 43:137; and Bahrani S, et al., *Prog. Clin. Biol. Res.*, 1995; 392:197). This condition is termed the "systemic inflammatory response syndrome" (SIRS). It may be self-limited or lead to a "multiple organ dysfunction syndrome" (MODS) (e.g., varying degrees of fever, hypoxemia, tachypnea, tachycardia, endothelial inflammation, myocardial insufficiency, hypoperfusion, altered mental status, vascular collapse, which may culminate in end-organ damage such as acute respiratory distress syndrome, coagulopathy, cardiac failure, renal failure, shock, and/or coma) (see: American College of Chest Physicians/Society of Critical Care Medicine Consensus Conference, *Crit. Care Med.*, 1992; 20:864; and Bone R C, *JAMA*, 1995; 273:155).

When SIRS is caused by infection, it is termed sepsis which, in turn, has progressively severe stages (severe sepsis, and septic shock). The diagnosis of sepsis does not obligate the demonstration of microorganisms, which may be presumed rather than demonstrated. Consequently, some authors subdivide the sepsis syndromes into "culture-positive" indicating that the causative microorganism(s) has(have) been identified, and "culture-negative" implying that the SIRS/sepsis is presumed to be caused by an infectious agent (see: Rangel-Fausto M S, et al., *JAMA*, 1995; 273:117). SIRS/sepsis is a self-perpetuating condition. Depending on the severity of the condition, the mortality rate averages 20–70%.

In the United States, nearly one-half million cases occur yearly; it has been estimated to represent the 13th leading cause of death, and is the major proximate cause of mortality in intensive care units (Centers for Disease Control, *MMWR*, 1990; 39:31; and Lowry S F, *Crit. Care Med.*, 1994; 22:S1–2).

Although the serum levels of certain proinflammatory cytokines tend to be higher with SIRS/sepsis, clinical trials have revealed a rather poor correlation between these levels and the degree of organ dysfunction, overall clinical course, or survival (Bone R C, *Crit. Care Med.* 1996; 24:163). Moreover, some cytokines may exist both in cell-associated and free forms, and only the latter are easily measured. Furthermore, because many cytokines have paracrine or autocrine functions, their levels may be elevated in local pools only and may not be detectable in the systemic circulation. Also, cytokines typically increase only transiently and may not be detected with a single serum sampling. Other rough correlates of sepsis include the acute-phase polypeptide, C-reactive protein, originating from the liver, and neopterin (Grabosch R, et al., Burns, 1992; 18–113), a heterocyclic metabolite produced by macrophages when they are stimulated by endotoxin or interferon-γ. Importantly, to date, there has been no reliable marker for the presence, the course, the response to therapy, or the prognosis of SIRS/sepsis (Bone R C, *Crit. Care Med.* 1996; 24:163).

It has become apparent that infectious diseases and SIRS/sepsis (with or without known infection) are often characterized by varying degrees of hyperprocalcitonemia; indeed, serum procalcitonin (ProCT) and/or some of its components can reach enormous levels (Becker K L, et al., *Anat. Rec.*, 1993; 236:136; Assicot M, et al., *Lancet*, 1993; 341:515; Becker K L, et al., "The hyperprocalcitonemia of severe infections," Endocrine Society, Washington, D.C., June 1995; and Becker K L, et al., "Hyperprocalcitonemia as a clinical marker for systemic inflammation," ICAAC, New Orleans, La., Sep. 16, 1996). Increased levels of ProCT and its components have been found in acute pulmonary illnesses, such as bacterial pneumonia or aspiration pneumonitis, that normalized with recovery. Patients with residual disease continued to have levels above normal (Becker K L, et al., *The Endocrine Lung in Health and Disease*, W B Saunders, Philadelphia, 1984; p. 277; and Nylen E S, et al., *Am. J. Med. Sci.* 1996; 312:12). Using specific antisera to ProCT, to the amino terminus of ProCT (nProCT), to calcitonin (CT), and to the calcitonin carboxyl peptide-I (CCP-I), in conjunction with HPLC and gel filtration techniques, it has been demonstrated that these patients have markedly increased serum levels of intact ProCT, nProCT, and usually the uncleaved CT:CCP-I peptide. However, mature CT usually remains normal or minimally elevated (Snider, R et al., "Characterization of the hyperprocalcitonemia of inflammatory/infectious disorders," Am. Fed. Clin. Res., New Orleans, La., Feb. 1, 1996; Becker, K L, et al., "The hyperprocalcitonemia of severe infections: Associated secretion of other constituents of the prohormone," Endocrine Society, Washington, D.C., Jun. 14–17, 1995).

Subsequently, in other infections (staphylococcus-induced toxic shock syndrome (Sperber S J, et al., *Rev. Inf. Dis.*, 1990; 12:736), bacterial meningitis (Assicot M, et al., *Lancet*, 1993; 341:515), melioidosis (Smith M D, et al., *Clin. Infect. Dis.*, 1995; 20:641), acute falciparium malaria (Davis T M E, et al., *Trans. Roy. Soc. Trop. Med. Hyg.*, 1994; 88:670), pyelonephritis (Becker K L, et al., "The hyperprocalcitonemia of severe infections," Endocrine Society, Washington, D.C., Jun. 14–17, 1995), etc.), serum ProCT levels as high as 200 ng/mL were reported. The SIRS which is secondary to pancreatitis (Becker K L, et al., Endocrine Society, Washington, D.C., June 1995; and White J., et al, *Pancreas Club*, San Francisco, Calif. May 19, 1996), burns (O'Neill W., et al, *J. Burn Care Rehab.*, 1992; 13:605; and Becker K., et al. *Anat. Rec.*, 1993; 236:136), and heat stroke (Nylen E S, et al., *Crit. Care Med. (In Press)*, 1997), also were found to manifest high serum levels of CT precursors (i.e., ProCT and/or its components).

In severe burns, greatly elevated levels of ProCT and/or its components were found, which correlated positively with mortality; these levels had considerable prognostic utility, sufficient to influence the type and aggressivity of therapy (Nylen E, et al., *Horm. Metab. Res.*, 1992; 24:439; and Nylen E S, et al., *Respir. Med.*, 1995; 89:41). It has since been determined that the high levels of CT precursor forms found in these patients consist mostly of ProCT, nProCT and the CT:CCP-I peptide, with mature CT being either normal or minimally elevated.

Interestingly, a linkage between endotoxin, inflammatory cytokines, and hyperprocalcitonemia was demonstrated by an experiment in which injection of endotoxin from *E. coli* bacteria into volunteers produced fever, chills and myalgia; serum TNFα increased to peak serum levels at 1½ hr, and Il-6 peaked at 6 hr (Dandona P, et al., *J. Cin. Endocrinol. Metab.*, 1994; 79:1605). Both of these cytokines then gradually normalized. Serum ProCT, initially undetectable, peaked at 6 hours (4.5 ng/mL), and thereafter maintained a plateau until at least 24 hr. Mature CT remained undetectable.

The conventional treatment of SIRS/sepsis varies according to the initiating cause (e.g., burns, infection, multitrauma, pancreatitis). Therapy may include cardiovascular support such as fluids and adrenergic agents, antibiotics, corticosteroids, respiratory assistance, oxygen, renal dialysis, etc. In addition, antibodies or antagonists to cytokines or endotoxin have been evaluated (Zeigler, E J, et al, *New. Engl. J. Med.*, 1991; 324:429; and Christman, J W, et al., *Crit. Care Med.*, 1995; 25:955). However, in spite of these therapies, SIRS and the sepsis syndromes continue to have an extremely high morbidity and mortality (Natanson, C, et al., *Ann Int Med*, 1994; 120:771; Suffredini, A F, *Crit. Care Med.*, 1994; 22:512; and Fisher, C J, et al, *New Eng. J. Med.*, 1996; 334:1697). Thus, there is no very effective method for preventing and/or treating SIRS, and there remains a very compelling need for alternative methods for preventing and/or treating SIRS/sepsis. There also remains a need for pharmaceutical compositions useful for preventing and/or treating SIRS/sepsis.

SUMMARY OF THE INVENTION

Accordingly, it is one object of the present invention to provide a novel method for preventing SIRS/sepsis.

It is another object of the present invention to provide a novel method for treating SIRS/sepsis.

It is another object of the present invention to provide novel compositions useful for preventing SIRS/sepsis.

It is another object of the present invention to provide novel compositions useful for treating SIRS/sepsis.

These and other objects, which will become apparent during the following detailed description, have been achieved by the inventors' discovery that administration, to a mammal, of an effective amount of an antibody specific for a component of procalcitonin, is effective for the prevention and/or treatment of SIRS/sepsis.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

Figure 1:
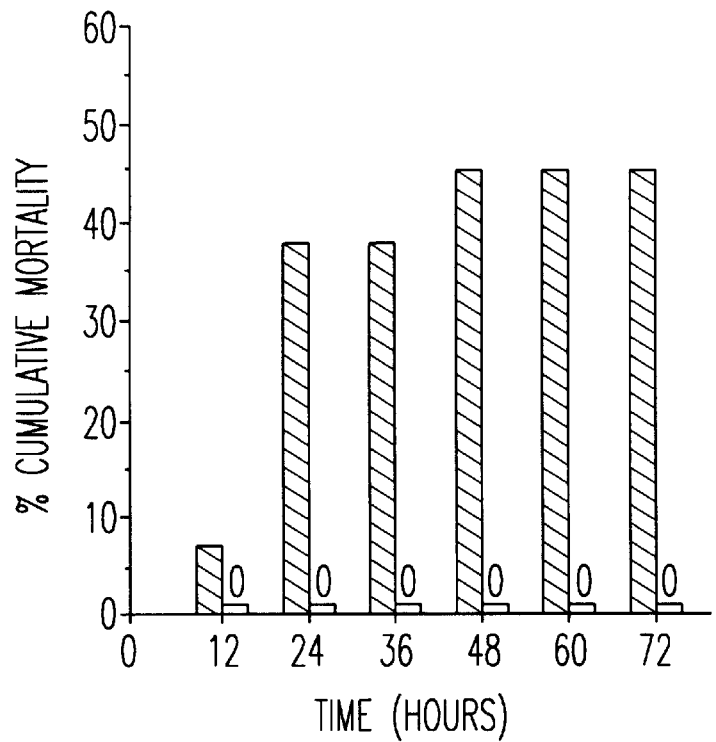
FIG. 1 illustrates the ability of an anti-ProCT antibody (in this case an antiserum to mature CT) to prevent death in hamsters with *E. coli* peritonitis.

DETAILED DESCRIPTION OF THE
PREFERRED EMBODIMENTS

Thus, in a first embodiment, the present invention provides a method for preventing and/or treating SIRS/sepsis by administering, to a human or other mammal in need thereof, an effective amount of an antibody reactive to procalcitonin or its component(s) (hereinafter referred to as antiprocalcitonin). In the context of the present invention, the term SIRS includes both sepsis and systemic inflammation from non-infectious sources. Thus, the present method is effective for the prevention and/or treatment of SIRS/sepsis resulting from bacterial, viral, parasitic, rickettsial, or fungal infection, and/or SIRS/sepsis resulting from any of a number of non-infectious causes (e.g., burns, pancreatitis, multitrauma, severe surgical trauma, transplant rejection, marked autoimmune reaction, ischemia reperfusion, transfusion reaction, heat stroke). In the context of the present invention, the term prevention also means the amelioration of the severity of SIRS/sepsis by administration prior to the onset of SIRS/sepsis.

Human calcitonin (CT) is a single-chain peptide consisting of 32 amino acid residues. The free, active, so-called "mature" CT hormone has an amidated proline at its carboxyl-terminus (Eipper B A, et al., *Annu. Neurosci.*, 1992; 15:57). The polypeptide precursor of CT is preprocalcitonin (Pre-ProCT), containing 141 amino acid residues. The CALC-I gene encodes the information for its primary structure (Becker K L, et al., in *Principles and Practice of Endocrinology and Metabolism*, $2^{nd}$ ed., Becker K L, Ed., J B Lippincontt Co., Philadelphia, 1995, p. 474). The 25 amino acid leader sequence assists the transport of the ribosomal precursor molecule into the cysternae of the rough endoplasmic reticulum; it is cleaved early in post-translational processing by a signal peptidase. The resultant prohormone, procalcitonin (ProCT; also termed PAN-116) consists of 116 amino acid residues (LeMoullec J M, et al., *FEBS Lett*, 1984; 167:93). At the amino terminus portion of ProCT, there is a 57-amino acid peptide called nProCT (also termed PAS-57). Immature CT is centrally placed within CT; it consists of 33 amino acid residues, including a carboxyl terminal glycine. The final 21-amino acid residues comprise the CT carboxyl terminal peptide-I (also termed PDN-21 or katacalcin). There also is an alternative form, present in much lower concentrations, termed CCP-II.

The biosynthetic secretory pathway for CT involves a complex series of modifications which eventuates in the final exocytosis of the mature secretory product. Topographically, in the neuroendocrine secretion of CT, the highly organized traffic from the endoplasmic reticulum passes through the Golgi apparatus, dense-core secretory vesicles, and, eventually the cell surface. This regulated secretory pathway for a CT molecule that is comprised mostly of the mature, bioactive form, differs from the constitutional, unregulated secretory pathway by which, in all likelihood, mostly ProCT is secreted (Burgess T C, et al., *Annu. Rev. Cell Biol.,* 1987; 243; Mostov K E, *Histol. Histopathol.,* 1995; 10:423; and Rothman J E, et al., *FASEB J.,* 1990; 4:1460). Although the mechanism by which the larger precursor, ProCT, is serially processed has not been entirely elucidated, the general outline is known. Proteolytic cleavages occur in the trans-Golgi and the secretory vesicles. The amidation process, which converts immature CT to its more active free mature form, probably occurs within the secretory vesicles (Steiner DF, et al., *J. Biol. Chem.,* 1992; 267:23435). In the regulated pathway, as occurs in neuroendocrine cells, these dense-core vesicles are destined to serve as storage repositories for later secretion; without the appropriate external stimulus, they have relatively long half-lives. Ultimately, in response to the appropriate signal at the plasma membrane, there is a brief increase of concentration of cytosol free $Ca^{+2}$ that induces exocytosis. In CT-secreting NE cells, the vesicles of the regulated pathway contain, in addition to mature CT, the nProCT, CCP-I, CT:CCP-I (Treilhou-Lahille F, et al., *Biology of the Cell,* 1986; 57–221), and perhaps CCP-II and CT:CCP-II peptides; most of these components are found, in very low concentrations, in the sera of normal persons (Becker, K L, et al., Procalcitonin and its constituent peptides circulate in normal persons, $15_{th}$ Joint Meeting of British Endocrine Societies, Dublin Ireland, Mar. 26, 1996).

The measurement of serum immunoreactive CT (iCT) has long been employed to detect and follow the course of the neoplasm of the thyroid C-cells, medullary thyroid cancer (MTC) (Becker K L, et al., *Acta Endocrinol.,* 1978; 89:89; and Becker K L et al., *Surg. Gynecol. Obstet.,* 1982; 154:897). Current immunoassays are fashioned so as to detect predominantly or exclusively the free, amidated, mature CT (Guilloteau D, et al., *J. Clin. Endocrinol. Metab.,* 1990; 71:1064; Motté P, et al., *Clin. Chim. Acta.,* 1988; 174:35; Seth R, et al., *Horm. Metab. Res. Suppl.,* 1989; 21:3; and Weissel M, et al., *Acta Endocrinol.,* 1991; 124:540); the most specific two-antisera capture assays used for this purpose probably do not detect ProCT or any of its other components. However, the use of region-specific antisera and separatory techniques has demonstrated that in addition to secreting considerable amounts of mature CT, MTC also secretes large amounts of ProCT and its components. In addition, two neoplasms of the lung, the malignant small cell lung cancer and the more benign bronchial carcinoid, which are putative tumors of CT-containing pulmonary neuroendocrine cells, often secrete immunoreactive CT (Becker K L, et al., in *Comparative Respiratory-Tract Carcinogenesis,* Reznick-Schuller H, Ed., CRC Press, Boca Raton, Fla., 1983; p. 161; and Becker K L, et al., *Biochem. Pharmacol.,* 1985; 34:155). A similar phenomenon of immunoreactive CT secretion occurs in some seemingly non-neuroendocrine tumors.

There is no particular limitation on the anti-procalcitonin antibody which can be used in the present invention. Furthermore, the anti-procalcitonin may be either a polyclonal antibody or monoclonal antibody, or a mixture thereof. The antibody may be to the intact ProCT or any of its components, i.e., the immature CT, mature CT, CCP-I, CCP-II, nProCT, or to any other fragments or amino acid sequence(s) of the known ProCT molecule, so long as it is able to bind to and neutralize procalcitonin. In the case of nonhuman mammals, the antibody may be to any component, fragment, or amino acid sequence of the respective procalcitonin structure of that mammal. The antibody also may be to amino acid or other chemical modifications of the human or mammalian molecular structure of ProCT or its component peptides or amino acid sequences.

Good results have been achieved using polyclonal antibodies. In another preferred embodiment, the anti-procalcitonin is a monoclonal antibody or a mixture of two or more monoclonal antibodies, or a mixture of monoclonal plus polyclonal antibodies. The suitability of the monoclonal or polyclonal antibody(ies) produced for use in the present invention may easily be determined in vitro (binding to ProCT or ProCT-component peptides). It may additionally be evaluated by means of the hamster model as described in the Examples below.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

Methods for producing polyclonal anti-polypeptide antibodies are well-known in the art. See U.S. Pat. No. 4,493, 795 to Nestor et al. A monoclonal antibody, typically containing Fab and/or $F(ab')_2$ portions of useful antibody molecules, can be prepared using the hybridoma technology described in *Antibodies—A Laboratory Manual,* Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with procalcitonin, calcitonin, etc.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to produce antibodies which immunoreact with procalcitonin.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Methods for producing monoclonal antibodies to such peptides as procalcitonin or its components are also well-known in the art. See Niman et al., *Proc. Natl. Acad. Sci. USA,* 80:4949–4953 (1983). Typically, the present procalcitonin or a peptide analog is used either alone or conjugated to an immunogenic carrier, as the immunogen in the before described procedure for producing anti-procalcitonin monoclonal antibodies. The hybridomas are screened for the ability to produce an antibody that immunoreacts with the procalcitonin peptide analog.

The anti-procalcitonin may be administered either intravenously, subcutaneously, intramuscularly, intrapleurally, intraperitoneally, orally, and/or rectally. When administered intravenously, the anti-procalcitonin is preferably in the form of a sterile saline, or other physiologic electrolyte solution. Similar diluents may be used for the other routes. Oral or rectal administration may require an adjuvant which augments absorption.

Although the exact dosage of anti-procalcitonin to be administered will depend on the patient's clinical condition and/or the observed increases in levels of serum procalcitonin (1 to 500 ng/mL), or of nProCT (500 to 250,000 pg/mL). The anti-procalcitation is suitably administered in an amount which is sufficient to bind, in vitro, 0.4 to 100 nmol of procalcitonin and/or its component peptides per kg of body weight of the patient, commonly 10 to 100 nmol of procalcitonin and/or its component peptides per kg of body weight. An occasional case may require a dose higher than that which is sufficient to bind, in vitro, 100 nmol of procalcitonin per kg of body weight of the patient.

The anti-procalcitonin may be administered in a single dose or given in 2 to 10 divided doses administered during the 24 hour period immediately subsequent to the clinical suspicion of imminent SIRS/sepsis or an infection or other illness or condition suspected or feared to eventuate in SIRS/sepsis. On 2–4 subsequent days, repeat doses may be administered once or in 2–4 divided doses, equivalent to a total daily dose of 25–100% of the total daily dose given on day one, dependent on the patient's clinical response. As therapy of diagnosed SIRS/sepsis, the anti-procalcitonin is administered in a similar manner. However, repeat dosing may be needed for many days if the patient is extremely ill and has clinical complications. Either as prevention or as therapy, relative to the intravenous route of injection, dosages for other routes would be 2× for intrapleural and intraperitoneal, 4× for intramuscular, 5× for subcutaneous, and 8× for oral and rectal.

Good results have been achieved in our laboratory model by the intraperitoneal administration of anti-procalcitonin sufficient to bind 9 to 10.5 nmol/kg procalcitonin in 2 to 5 divided doses during the 24 hr following the beginning of sepsis, subsequently administering booster doses as needed.

As noted above, the present method is useful for preventing and/or treating SIRS/sepsis. The administration of anti-procalcitonin may be commenced in cases of suspected or early stages of infection or SIRS, or after the onset of overt SIRS/sepsis. Furthermore, the onset may be determined by fulfillment of the criteria of the definition of SIRS. Other findings, which may or may not be present, may include the presence of bacteria in the blood, increased levels of procalcitonin or its components in the blood; increased serum, salivary or urine levels of cytokines; or increased serum levels of C-reactive protein, or serum endotoxin, or serum or urine neopterin. Alternatively, the anti-procalcitonin administration may be commenced prior to the actual onset of SIRS/sepsis to a patient or subject who is at risk for developing sepsis or severe systemic inflammation (e.g., only one of the prior-referenced criteria of SIRS, or after a burn, trauma, extensive surgery, transfusion reaction, graft/ organ rejection, heat stroke, heat exhaustion, pancreatitis, or a known or suspected infection).

Subjects who are at risk of developing SIRS or sepsis include newborn babies and infants, the elderly, the immunocompromised patient (e.g., a patient receiving corticosteroids or chemotherapy, a patient with the acquired immunodeficiency syndrome), or, as mentioned above, in persons with burns, infection, heat stroke, pancreatitis, severe autoimmune disease, transfusion reaction, extensive surgery, graft/organ rejection, or pancreatitis.

When used therapeutically, the anti-procalcitonin antibody should be administered as soon as a patient with the onset of infection or SIRS/sepsis has been identified. Subsequent doses may be administered once to twice daily until the patient shows clinical indications of recovery, and/or a markedly decreased blood level of procalcitonin or its components, and/or a decrease of blood, urine or salivary levels of cytokines, of C-reactive protein, of neopterin, or of endotoxin. Based upon the clinical and/or laboratory findings (such as leukocyte count, cytokine levels, ProCT levels and/or ProCT component levels), doses may be administered more frequently or less frequently.

When used preventively, as soon as a patient with the aforementioned risks has been identified, he or she should receive the anti-procalcitonin antibody. It should be repeated once or twice daily until clinical and aforementioned laboratory criteria indicate that the patient is no longer at risk of developing SIRS/sepsis. Based upon the clinical and/or the serum levels of ProCT or its components, and/or the prior-mentioned clinical and laboratory parameters, doses may be administered more frequently or less frequently.

When used either preventively or therapeutically, the anti-procalcitonin antibody may be administered intravenously, subcutaneously, intramuscularly, intraperitoneally, intrapleurally, orally, rectally, or by combinations thereof. The administration may be intermittent or continuous (e.g., continuous intravenous infusion).

When used either preventively or therapeutically, the anti-procalcitonin antibody may be administered with other agents such as corticosteroids, thyroid hormone, and/or antibiotics, and/or cytokine antagonists and/or anti-cytokine antibodies, and/or endotoxin antagonists or anti-endotoxin antibodies; and/or may be administered with any other therapy known or suspected to be beneficial to treat SIRS/ sepsis or to avert its onset.

Although not intending to be bound by any theory or mechanism, the present inventors provide the following comments on the phenomena underlying the present invention.

There is increasing evidence for biological activity of some prohormones and their components in addition to the classical mature hormone to which they give rise. Prior to the present invention, the impact of hyperprocalcitonemia on the patient with infection or SIRS/sepsis was unknown. SIRS/sepsis is commonly associated with multiple symptomatic, clinical, and metabolic manifestations and some of them (such as hyperglycemia and hypocalcemia), may, perhaps, be attributable to the effects of procalcitonin and/or its components.

HPLC on sera of SIRS patients has been performed to determine whether the hypersecretion of ProCT in SIRS is a phenomenon common to other prohormones as well: increased serum levels of ProCGRP or mature CGRP were not detected. Also, since endotoxin and cytokines can acutely stimulate the hypothalamic-pituitary-adrenal axis (Mastorakos G, et al., *J. Clin. Endocrinol. Metab.,* 1994; 79:934), serum proopiomelanocortin (POMC) was measured (two-antibody sandwich technique), and was normal, as was serum ACTH.

The cause of the hypersynthesis of ProCT is not apparent. The immediate signal may be a factor, perhaps primarily or secondarily due to a cytokine, which induces an intranuclear message. Alternatively, the CT gene may contain a regulatory region common to inflammatory mediators (Schutze, S, et al., *Immunobiology*, 1995; 193:193). One might postulate a scenario in which a greatly stimulated hypersynthesis of ProCT produced by CT-secreting neuroendocrine cells overwhelms their endoproteolytic machinery. If neuroendocrine tissue is the source, such an extraordinarily augmented and ongoing hypersecretion of ProCT and its components in the face of a normal serum level of mature CT suggests not only hypersynthesis, but also a marked shift to the constitutive pathway of secretion, resulting in an incomplete processing of precursors.

The constitutive secretory pathway is present in all cells; here, the vesicles which bud off from the trans-Golgi are much less dense than those of the regulated pathway, and migrate rapidly to the plasma membrane. Hence, in contrast to the slow transit-time of the dense vesicles of the regulated system, which await periodic stimuli for exocytosis, the constitutive pathway vesicles are involved in a non-storing, bulk-flow continuous secretion of newly synthesized peptide(s); the vesicles fuse continuously with the plasma membrane, and the extrusion of their hormonal material may be calcium independent.

If the source of the ProCT is neuroendocrine cells, there may be either an increased transcription of its gene or, post-transcriptionally, an increased stability of its mRNA. If it is regulated at the transcriptional level, it may be acting on possible enhancer-like sequences in the ProCT gene promoter. In either case, the major factor determining the exceptional predominance of prohormonal forms would likely be the choice of the trans-Golgi to route to the constitutive pathway, thus bypassing much of the enzymatic processing (Burgess TC, et al., *Annu. Rev. Cell Biol.*,1987; 243; and Rothman J E, et al., *FASEB J.*, 1990; 4:1460).

Experimentally, such a shift to constitutional secretion has been shown to occur by the induction of dysfunctional prohormone convertase enzymes, by the loss of Golgi recognition molecules, by diminished intracellular calcium, by alkalinization of cytoplasmic organelles, or by depolarization of the plasma membrane. In this regard, some cytokines may indeed be able to induce constitutive secretion due to membrane depolarization (Mostov K E, *Histol. Histopathol.*, 1995; 10:423; and Madara J L, et al., *J. Clin. Invest.*, 1989; 83:724).

However, it is quite possible that these enormous serum levels of ProCT in infection or SIRS/sepsis do not originate from neuroendocrine cells, either exclusively, or perhaps, at all. In this respect, hyperprocalcitonemia of SIRS/sepsis can occur in the absence of the thyroid gland, a structure that produces an appreciable amount of the serum immunoreactive CT of normal persons (Assicot M, et al., *Lancet*, 1993; 341:515). Also, it is well known that some hormonal peptides, which are normally secreted by neuroendocrine cells, are contained within other presumably non-neuroendocrine cells, albeit at low levels (Krieger D T, *Clin. Res.*, 1983; 3:342; and LeRoith D, et al., *Adv. Metabolic Disorders*, 1983; 10:303). Non-neuroendocrine cells presumably possess cell-type regulatory mechanisms limiting expression of ProCT mRNA. It is conceivable that this mechanism is deregulated by unusually high levels of a SIRS-related secretagogue. Stimulation of synthesis in such non-neuroendocrine cells would preferentially induce ProCT secretion because they lack the enzymes for complete prohormonal processing.

Other features of the invention will become apparent in the course of the following descriptions of exemplary embodiments which are given for illustration of the invention and are not intended to be limiting thereof.

EXAMPLES

Materials and Methods

Animals

Golden Syrian Hamsters—100 g were housed in a controlled environment and were exposed to 12 hour, light-dark cycles. The animals were given unrestricted access to water and standard rodent chow. This study was approved by the Institutional Animal Care and Use Committee at the Veterans Affairs Medical Center, Washington, D.C.

Bacteria

*Escherichia coli* (O018:K1:H7) was obtained from Dr. Alan S. Cross, Division of Communicable Diseases and Immunology, Walter Reed Army Institute of Research, Washington, D.C. It was grown in 100 ml of L B Broth (Fischer Scientific) at 37° C. in a shaker water bath to log phase and stored in 250 $\mu$l aliquots at $-70°$ C. until use.

Intra-abdominal pellets

*Escherichia coli* were prepared by growing a frozen aliquot of bacteria to log phase, quantitating the colonies via spectrophotometry, diluting the stock to $1.0 \times 10^9$ cfu/ml and serially plating appropriate dilutions for confirmation. Pellets for intra-abdominal challenge were made by adding 0.5 ml of an *Escherichia coli* suspension to 0.5 ml of sterile molten agar at 50° C. and allowing the mixture to solidify at room temperature in an 8 mm plastic imbedding mold. The final number of viable colony forming units of bacteria in each infected pellet was $5.0 \times 10^8$.

Induction of Peritonitis

The method for inducing peritonitis has been reported: (Dunne, J R, et al., *J. Surg. Res.*, 1996; 61:348; and Steinwald, P, et al., Intl. Congress Endocrinology, San Francisco, Calif., June 1996). Bacterial peritonitis was then produced by intraperitoneal implantation of the infected agar pellets. After anesthetizing each animal with 50 mg/kg pentobarbital, i.p. and prepping the abdomen with 70% alcohol, the peritoneal cavity was opened via a midline incision. An infected agar pellet was placed in the right lower quadrant and the incision was closed in two layers with a running 4-O nylon suture. Each animal was given a single, intramuscular injection of ceftriaxone (14.3 mg/kg, Roche, Nutley, N.J.) and was placed in a separate cage to recover from anesthesis. Water and rat chow were again provided ad libitum.

Antibodies

1-Ethyl-3-(3-dimethylaminopropyl)carbodiimide, hydrochloride, 8 mg, was used to couple 4 mg synthetic human calcitonin (Organon), to 16 mg hemocyanin (keyhole limpet, Calbiochem, La Jolla, Calif.). The dialyzed conjugate, 17 mg, was suspended in 10 mL of 0.154 M NaCl. Initially, and at 2 weeks, a 25 kg goat received multiple intradermal injections on its back of an emulsion consisting of 1 mL of the conjugate suspension and 1 mL complete Freund's adjuvant. The goat also received a subcutaneous injection of 0.5 mL pertussis vaccine. Antibody to calcitonin/procalcitonin was detectable within one month of the first injection. Subsequent booster injections (multiple intradermal sites on the back), given at monthly intervals, consisted of an emulsion containing 0.5 mL of the conjugate suspension and 0.5 mL of incomplete Freund's Adjuvant (lanolin). Subcutaneous booster injections of 0.5 mL pertussis vaccine were also administered. The booster injections were discontinued after 5 months and resumed when the titer began to decline at 9 months. The antiserum bleedings chosen for neutralization studies (bleedings 12–26) were collected between 5 and 20 months. The estimated titers of these antisera, which were multiregion specific for calcitonin, ranged from 1:500,000 to 1:2,000,000.

Example 1
Prevention of Mortality

Peritonitis was induced in 32 Golden Syrian Hamsters as described in the Materials and Methods section. At 0 and 24 hr, the experimental animals (n=16) received intraperitoneal injections of the anti-CT multiregion specific goat polyclonal antiserum (titer of 1:1,000000), capable of detecting hamster mature CT and ProCT in radioimmunoassays, and prepared as described in the Materials and Methods section. Controls (n=16) received non-immune goat serum. There was no mortality in the experimental group in 72 hours despite 45% mortality in the control group (p<0.004). The results are presented graphically in FIG. 1. The solid bars represent the cumulative mortality of the control group of hamsters which did not receive antibodies reactive to procalcitonin and the open bars represent the cumulative mortality of the experimental group which received antibodies reactive to procalcitonin. In view of the remarkable effectiveness of antiserum treatment, the experimental group was followed for another 60 hr, during which time only one of the treatment animals died. Furthermore, mortality was also reduced when the initial intraperitoneal antiserum injection was delayed until 3 hr after *E. coli* implantation.

The statistical significance of the data at each time is shown in the following table:

| Time (hr) | p < |
|---|---|
| 12 | 0.448 |
| 24 | 0.011 |
| 48 | 0.004 |
| 72 | 0.004 |

Example 2
Therapy of Sepsis

Figure 2:
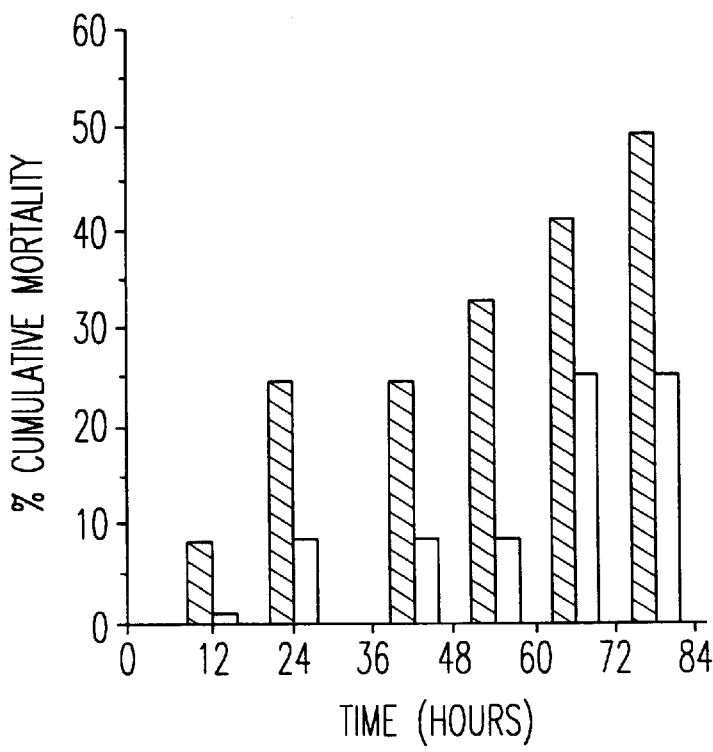
FIG. 2 shows the ability of anti-CT antibody to reduce the mortality rate in hamsters when administered after the induction of *E. coli* peritonitis with five intraperitoneal injections at 1, 3, 6, 12, and 24 hours after the induction of peritonitis.

The experiment described in Example 1 was repeated with the exception that the experimental animals (n=12) received intraperitoneal injections of the anti-CT multiregion specific goat polyclonal antiserum (titer of 1:1,000,000) at 1, 3, 6, 12, and 24 hours after the induction of peritonitis. The control animals (n=12) received no anti-CT antiserum. The results are shown in FIG. 2. The statistical significance of the data at each time is shown in the following table:

| Time (hr) | p < |
|---|---|
| 12 | 1 |
| 24 | 0.342 |
| 36 | 0.342 |
| 48 | 0.317 |
| 60 | 0.430 |
| 72 | 0.245 |

Example 3
Therapy of Sepsis

Figure 3:
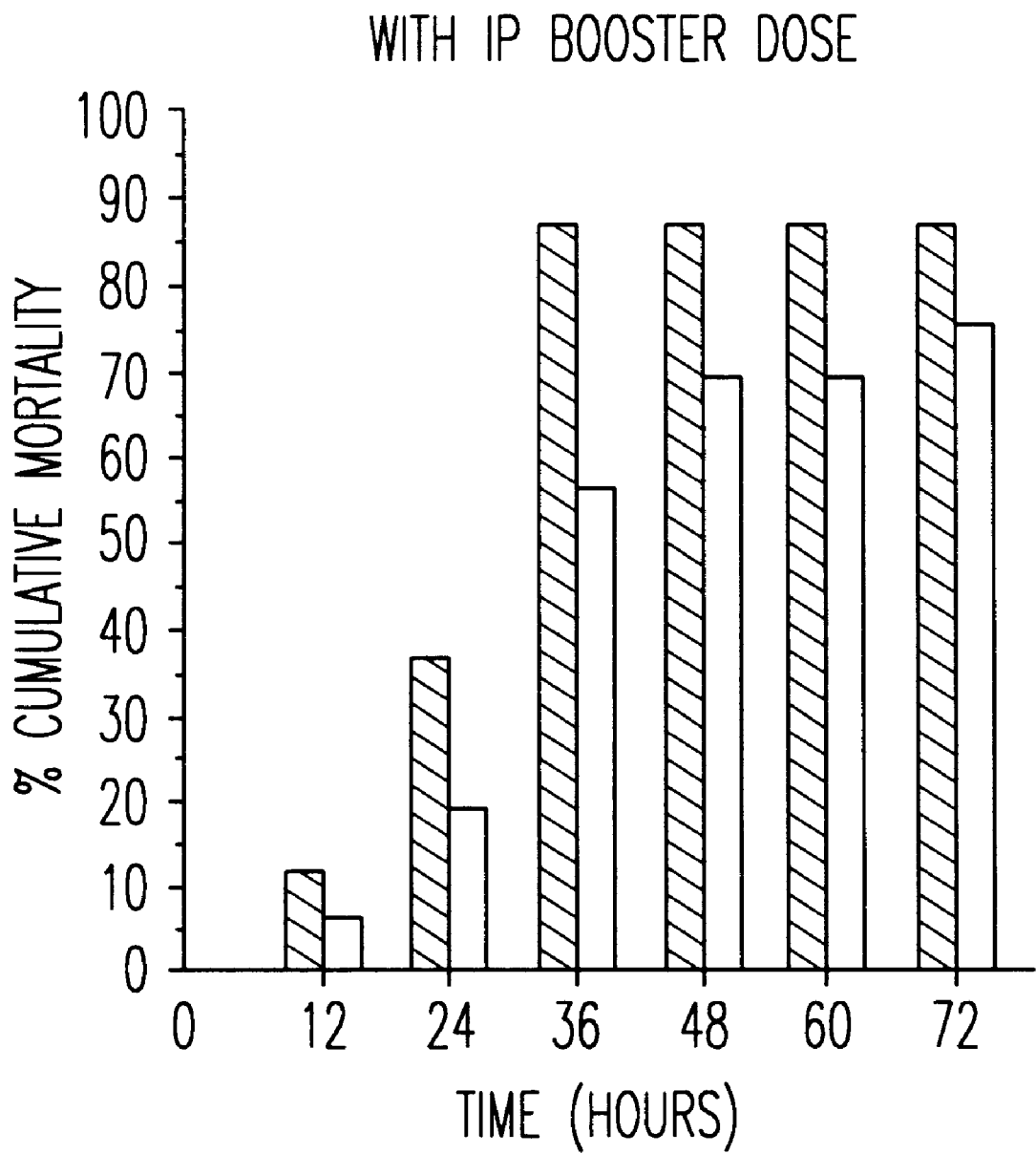
FIG. 3 shows the ability of anti-CT antibody to reduce the mortality rate in hamsters when administered after the induction of *E. coli* peritonitis with two intraperitoneal injections at 3 and 24 hours after the induction of peritonitis.

The experiment described in Example 1 was repeated with the exception that the experimental animals (n=16) received intraperitoneal injections of the anti-CT multiregion specific goat polyclonal antiserum (titer of 1:1,000,000) at 3 and 24 hours after the induction of peritonitis. The control animals (n=16) received no anti-CT antiserum. The results are shown in FIG. 3. The statistical significance of the data at each time is shown in the following table:

| Time (hr) | p < |
|---|---|
| 12 | 1 |
| 24 | 0.42 |
| 36 | 0.113 |
| 48 | 0.222 |
| 60 | 0.222 |
| 72 | 0.481 |

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. A method for treating systemic inflammatory response syndrome including sepsis (SIRS/sepsis), comprising administering, to a mammal in need thereof, an effective amount of an antibody which neutralizes procalcitonin, wherein said mammal is suffering from SIRS/sepsis induced by bacterial infection.

2. The method of claim 1, wherein said antibody is a polyclonal antibody.

3. The method of claim 1, wherein said antibody is a monoclonal antibody.

4. The method of claim 1, wherein said antibody comprises multiple monoclonal, multiple polyclonal antibodies, or a combination of monoclonal and polyclonal antibodies.

5. The method of claim 1, wherein said mammal is a human.

6. The method of claim 1, wherein said mammal is selected from the group consisting of cats, dogs, cows, horses, and pigs.

7. The method of claim 1, wherein said antibody is administered intravenously, subcutaneously, intramuscularly, intraperitoneally, within the pleural cavity, orally or rectally.

8. The method of claim 1, wherein said antibody is administered in an amount sufficient to neutralize, in vitro, 0.4 to 100 nmol/kg of procalcitonin.

9. The method of claim 1, wherein said antibody is administered in an amount sufficient to neutralize, in vivo, 0.4 to 100 nmol/kg of procalcitonin.

10. The method of claim 1, wherein said mammal is suffering from SIRS/sepsis resulting from pneumonia/pneumonitis infection.

11. The method of claim 1, wherein said mammal is suffering from SIRS/sepsis resulting from toxic shock syndrome.

12. The method of claim 1, wherein said bacterial infection is culture positive.

13. The method of claim 1, wherein said bacterial infection is culture negative.

14. A method of reducing the risk of dying from systemic inflammatory response syndrome including sepsis (SIRS/sepsis) induced by bacterial infection, comprising administering, to a mammal in need thereof, an effective amount of an antibody which neutralizes procalcitonin, wherein said mammal is suffering from bacterial infection.

15. The method of claim 14, wherein said antibody is a polyclonal antibody.

16. The method of claim 14, wherein said antibody is a monoclonal antibody.

17. The method of claim 14, wherein said antibody comprises multiple monoclonal, multiple polyclonal antibodies, or a combination of monoclonal and polyclonal antibodies.

18. The method of claim 14, wherein said mammal is a human.

19. The method of claim 14, wherein said mammal is selected from the group consisting of cats, dogs, cows, horses, and pigs.

20. The method of claim 14, wherein said antibody is administered intravenously, subcutaneously, intramuscularly, intraperitoneally, within the pleural cavity, orally or rectally.

21. The method of claim 14, wherein said antibody is administered in an amount sufficient to neutralize, in vitro, 0.4 to 100 nmol/kg of procalcitonin.

22. The method of claim 14, wherein said antibody is administered in an amount sufficient to neutralize, in vivo, 0.4 to 100 nmol/kg of procalcitonin.

23. The method of claim 14, wherein said mammal is suffering from pneumonia/pneumonitis infection.

24. The method of claim 14, wherein said mammal is suffering from toxic shock syndrome.

25. The method of claim 14, wherein said bacterial infection is culture positive.

26. The method of claim 14, wherein said bacterial infection is culture negative.

* * * * *